(12) United States Patent
Eggers (10) Patent No.: US 10,383,718 B2
(45) Date of Patent: Aug. 20, 2019

(54) ABSORBABLE VASCULAR FILTER (71) Applicant: Adient Medical, Inc., Pearland, TX (US)

(72) Inventor: Mitchell Donn Eggers, Pearland, TX (US)

(73) Assignee: ADIENT MEDICAL, INC., Pearland, TX (US)

( * ) Notice: Subject to any disclaimer, the term of this patent is extended or adjusted under 35 U.S.C. 154(b) by 84 days.

(21) Appl. No.: 15/174,973

(22) Filed: Jun. 6, 2016

(65) Prior Publication Data
US 2016/0324622 A1  Nov. 10, 2016

Related U.S. Application Data

(63) Continuation of application No. 13/036,351, filed on Feb. 28, 2011, now abandoned.

(51) Int. Cl.
*A61F 2/01* (2006.01)

(52) U.S. Cl.
CPC .......... *A61F 2/01* (2013.01); *A61F 2002/011* (2013.01); *A61F 2002/016* (2013.01); *A61F 2210/0004* (2013.01); *A61F 2220/0016* (2013.01); *A61F 2230/0006* (2013.01); *A61F 2230/008* (2013.01); *A61F 2230/0021* (2013.01); *A61F 2310/00017* (2013.01); *A61F 2310/00023* (2013.01); *A61F 2310/00029* (2013.01);
(Continued)

(58) Field of Classification Search
CPC ...... A61F 2/01; A61F 2/013; A61F 2002/016; A61F 2002/018; A61B 2017/12168

USPC .......................................... 606/200; 623/1.38
See application file for complete search history.

(56) References Cited

U.S. PATENT DOCUMENTS 4,425,905 A   1/1984  Simon
4,655,771 A   4/1987  Wallsten
(Continued)

FOREIGN PATENT DOCUMENTS

CA   2093599 A1   10/1993
CA   2710001 A1    7/2009
(Continued)

OTHER PUBLICATIONS

Supplementary European Search Report issued in corresponding European Application No. 12752614, dated Nov. 10, 2016 (7 pages).
(Continued)

*Primary Examiner* — Martin T Ton
(74) *Attorney, Agent, or Firm* — Pillsbury Winthrop Shaw Pittman LLP (57) ABSTRACT

An absorbable vascular filter is disclosed for deployment within a vessel for temporary filtering of body fluids. A preferred embodiment is the placement of such absorbable vascular filter within the inferior vena cava (IVC) to filter emboli for the prevention of pulmonary embolism for a limited duration in time. Once protection from PE is complete, the filter is sequentially biodegraded according to a planned schedule determined by the absorption properties of the filter components. Hence the temporary absorbable vascular filter obviates the long term complications of permanent IVC filters such as increased deep vein thrombosis, while also circumventing the removal requirement of metal retrievable IVC filters.

13 Claims, 3 Drawing Sheets

(52) U.S. Cl.
CPC .............. *A61F 2310/00071* (2013.01); *A61F 2310/00095* (2013.01); *A61F 2310/00131* (2013.01); *A61F 2310/00149* (2013.01)

(56) References Cited

U.S. PATENT DOCUMENTS

| | | | |
|---|---|---|---|
| 4,817,600 A | 4/1989 | Herms et al. | |
| 5,317,612 A | 5/1994 | Bryan et al. | |
| 5,350,398 A * | 9/1994 | Pavcnik | A61F 2/01 606/200 |
| 5,375,612 A * | 12/1994 | Cottenceau | A61F 2/01 128/899 |
| 5,443,498 A | 8/1995 | Fontaine | |
| 5,591,199 A | 1/1997 | Porter et al. | |
| 5,626,605 A | 5/1997 | Irie et al. | |
| 6,127,600 A | 10/2000 | Beach et al. | |
| 6,146,404 A | 11/2000 | Kim et al. | |
| 6,159,142 A | 12/2000 | Alt | |
| 6,245,103 B1 * | 6/2001 | Stinson | A61F 2/90 623/1.22 |
| 6,258,026 B1 | 7/2001 | Ravenscroft et al. | |
| 6,267,776 B1 | 7/2001 | O'Connell | |
| 6,497,709 B1 | 12/2002 | Heath | |
| 6,506,205 B2 | 1/2003 | Goldberg et al. | |
| 6,517,559 B1 | 2/2003 | O'Connell | |
| 6,582,447 B1 | 6/2003 | Patel et al. | |
| 6,620,183 B2 | 9/2003 | Dimatteo | |
| 6,652,558 B2 | 11/2003 | Patel et al. | |
| 6,658,558 B1 | 12/2003 | Kahle | |
| 6,792,979 B2 | 9/2004 | Konya et al. | |
| 6,932,832 B2 | 8/2005 | Patel et al. | |
| 6,972,025 B2 | 12/2005 | WasDyke | |
| 7,001,424 B2 | 2/2006 | Patel et al. | |
| 7,261,731 B2 | 8/2007 | Patel et al. | |
| 7,279,005 B2 | 10/2007 | Stinson | |
| 7,582,108 B2 | 9/2009 | Hierlemann et al. | |
| 8,162,970 B2 | 4/2012 | Gilson et al. | |
| 2001/0021871 A1 | 9/2001 | Stinson | |
| 2003/0014127 A1 | 1/2003 | Talja et al. | |
| 2003/0040771 A1 | 2/2003 | Hyodoh et al. | |
| 2003/0139765 A1 | 7/2003 | Patel et al. | |
| 2003/0153945 A1 | 8/2003 | Patel et al. | |
| 2003/0163159 A1 | 8/2003 | Patel et al. | |
| 2003/0176888 A1 | 9/2003 | O'Connell | |
| 2003/0199918 A1 | 10/2003 | Patel et al. | |
| 2004/0059373 A1 | 3/2004 | Shapiro et al. | |
| 2004/0138738 A1 | 7/2004 | Stinson | |
| 2004/0193209 A1 | 9/2004 | Pavcnik et al. | |
| 2005/0143805 A1 | 6/2005 | Hierlemann et al. | |
| 2005/0267512 A1 | 12/2005 | Osborne et al. | |
| 2005/0267515 A1 | 12/2005 | Oliva et al. | |
| 2006/0025852 A1 * | 2/2006 | Armstrong | A61B 17/12022 623/1.17 |
| 2006/0206138 A1 | 9/2006 | Eidenschink | |
| 2006/0241675 A1 | 10/2006 | Johnson et al. | |
| 2007/0032816 A1 | 2/2007 | O'Connell et al. | |
| 2007/0093744 A1 | 4/2007 | Elmaleh | |
| 2007/0112372 A1 | 5/2007 | Sosnowski et al. | |
| 2008/0027481 A1 * | 1/2008 | Gilson | A61F 2/01 606/200 |
| 2008/0107744 A1 | 5/2008 | Chu | |
| 2008/0119886 A1 | 5/2008 | Greenhalgh | |
| 2008/0269871 A1 | 10/2008 | Eli | |
| 2009/0099643 A1 | 4/2009 | Hyodoh et al. | |
| 2009/0105747 A1 | 4/2009 | Chanduszko et al. | |
| 2009/0187210 A1 | 7/2009 | Mackiewicz | |
| 2009/0192543 A1 | 7/2009 | Wasdyke | |
| 2009/0299403 A1 | 12/2009 | Chanduszko et al. | |
| 2010/0016881 A1 | 1/2010 | Fleck et al. | |
| 2010/0042135 A1 | 2/2010 | Shirley et al. | |
| 2010/0087908 A1 | 4/2010 | Hilaire et al. | |
| 2010/0174310 A1 | 7/2010 | Tessmer | |
| 2010/0256669 A1 * | 10/2010 | Harris | A61F 2/01 606/200 |
| 2010/0268262 A1 | 10/2010 | Balar | |
| 2011/0106234 A1 | 5/2011 | Grandt | |
| 2011/0213404 A1 * | 9/2011 | Binkert | A61F 2/01 606/200 |
| 2012/0245620 A1 | 9/2012 | Gilson et al. | |
| 2012/0259402 A1 | 10/2012 | Grandt | |
| 2012/0277787 A1 | 11/2012 | Eggers | |

FOREIGN PATENT DOCUMENTS

| | | |
|---|---|---|
| CN | 101945675 A | 1/2011 |
| EP | 0894505 A2 | 2/1999 |
| EP | 1574169 A2 | 9/2005 |
| EP | 1574169 A3 | 9/2005 |
| EP | 1582178 A2 | 10/2005 |
| JP | 2002535075 A | 10/2002 |
| JP | 2008508073 A | 3/2008 |
| JP | 2009518122 A | 4/2009 |
| JP | 2009543655 A | 12/2009 |
| WO | 1996017634 A2 | 6/1996 |
| WO | 2000044308 A2 | 8/2000 |
| WO | 2006020425 A1 | 2/2006 |
| WO | 2007067451 A2 | 6/2007 |
| WO | 2008010197 A2 | 1/2008 |
| WO | 2009/085548 A2 | 7/2009 |
| WO | 2009085548 A2 | 7/2009 |
| WO | 2010/077973 A2 | 7/2010 |
| WO | 2010077973 A2 | 7/2010 |

OTHER PUBLICATIONS

Zhenling, J, et al., "Type of hernia repair material, research work development and application selection", Journal of Southeast University (Medical Science Edition), 2009, 5(28):451-454.

English Machine Translation of Abstract by Google for Zhenling, J, et al., "Type of hernia repair material, research work development and application selection", Journal of Southeast University (Medical Science Edition), 2009, 5 (28):451-454.

Australian Government Intellectual Property Office, Patent Examination Report No. 1 dated Jan. 30, 2015.

Eggers, M., et al., In Vitro Analysis of Polymer Candidates for the Development of Absorbable Vascular Filters, J. Vasc. Interv. Radiol., 2012, 23:1023-1030.

International Application No. PCT/US2012/026398, International Search Report dated May 24, 2012.

JR Eriksen et al., Choice of Mesh for Laparaoscopic Ventral Hernia Repair, Hernia (2007) 11:481-492).

Notification of Reasons for Refusal Korean Patent Application No. 10-2013-7025601 dated Nov. 20, 2017 with English translation.

Examination Report No. 2 Australian Patent Application No. 2016200592 dated Jul. 20, 2017.

U.S. Non-Final Office Action dated Sep. 26, 2018 for U.S. Appl. No. 13/403,790.

Japanese Intellectual Property Office, Office Action dated Feb. 13, 2018, pp. 1-5.

Canadian Intellectual Property Office, Office Action dated Dec. 6, 2017, pp. 1-4.

Eggers et al., In Vitro Analysis of Polymer Candidates for the Development of Absorbable Vascular Filters, J. Vasc. Interv. Radiol., Aug. 2012, vol. 23, Issue 8, pp. 1023-1030.

Dabbagh O, Nagam N, Chitima-Matsiga R, et al. Retrievable inferior vena cava filters are not getting retrieved Where is the gap? Thrombosis Rsch 2010. 126: 493-497.

Goldhaber S Z, Ortel T L The Surgeon General's Call to Action to Prevent Deep Vein Thrombosis and Pulmonary Embolism, Office of the Surgeon General (US), National Heart, Lung, and Blood Institute (US),Rockville (MD), 2008, pp. 1-42.

Spencer F A, Emery C, Lessard D, Anderson F, Emani S, Aragam J et al., "The Worcester Venous Thromboembolism study; A Population-Based Study of the Clinical Epidemiology of Venous Thromboembolism", J Gen Intern Med Jul. 2006; 21 (7); pp. 722-727.

Bick R L., "Hereditary and acquired thrombophilia: preface", Seminars in Thrombosis and Hemostasis, 1999; vol. 25, No. 3, pp. 251-253.

(56) References Cited

OTHER PUBLICATIONS

Agudelo J F, Morgan S J, Smith W R., "Venous Thromboembolism in Orthopedic Trauma Patients", Orthopedics. Oct. 2005; 28(10):1164-1171.
Tapson V F., "Acute pulmonary embolism", N Engl J Med, 2008, 358, 10. pp. 1037-1052.
Goldhaber S Z, Visani L, De Rosa M. "Acute P E: clinical outcomes in the International Cooperative Pulmonary Embolism Registry (ICOPER)", Lancet 1999. 353. pp. 1386-1389.
Geerts W H, Jay R M, Code KI, et al. "A comparison of low-dose heparin with low-molecular weight heparin as prophylaxis against venous thromboembolism after major trauma", N Engl J. Med. 1996; 335:701-707.
Silverstein D M, Heit J A, Mohr D N, Petterson T M, O'Fallon W M, Meltron L J, 3rd. "Trends in the incidence of deep vein thrombosis and pulmonary embolism: a 25-year population-based study", Arch Intern Med 1998; 158(6). 585-593.
Von V R. Weitereuntersuchungenueber die verstopfung der lungenarterien and ihrefolge. Traube's Beitraegeexp Path u Physiol, 1846; 2:21-31.
Goldhaber S Z, Savage D D, Garrison R J, et al. Risk factors for pulmonary embolism: The Framingham Study. Am J. Med. 1983; 74: 1023-1028.
Coon W W. Epidemiology of venous thromboembolism. Ann Surg. 1977; 186:149-164.
Muntz J E, Michota F A. Prevention and management of venous thromboembolism in the surgical patient: options bye surgery type and individual patient risk factors, Am J of Surg, 2010; 199, S11-20.
American Academy of Orthopaedic Surgeons Clinical Guideline on Prevention of Pulmonary Embolism in Patients Undergoing Total Hip or Knee Arthroplasty, American Academy of Orthopaedic Surgeons, May 2007, pp. 1-63.
Pulmonary Embolism Prevention (PEP) Trial Collaborative Group: Prevention of pulmonary embolism and DVT with low dose aspirin: pulmonary embolism prevention (PEP) trial. Lancet. 2000; 355: pp. 1295-1302.
Prins M H, Hutten B A, Koopman M M, et al. Longterm treatment of venous thromboembolic disease. Thromb Haemost 1999;82:892-898.
Tran H, McRae S, Ginsberg J. Anticoagulant Treatment of Deep Vein Thrombosis and Pulmonary Embolism. Cardiology Clinics, 2008, 26, 235-250.
Morgan S J, Jeray K J, Phieffer L S, Grisby J H, Bosse M J, Kellam J F. Attitudes of orthopaedic trauma surgeons regarding current controversies in the management of pelvic and acetabular fractures. J Orthop Trauma. 2001; 15:526-532.
Meissner M H, Chandler W L, Elliot J S. Venous thromboembolism in trauma: a local manifestation of systemic hypercoagulability? J. Trauma 2003; 4:224-231.
Geerts W H, Bergqvist D, Pineo G F, et al. Prevention of venous thromboembolism: American College of Chest Physicians evidence-based clinical practice guidelines (8th edition). Chest 2008; 133:381S-453S.
Huo M H, Spyropoulos A C. The eighth American college of chest physicians guidelines on venous thromboembolism prevention: implications for hospital prophylaxis strategies. J Thromb Thrombolysis. Feb. 2011; 31(2): 196-208.
Baglin T P, Brush J, Streiff M. Guidelines on the use of vena cava filters. British Committee for Standard in Haematology, British J of Haematology, 2006, 134, 590-595.
Rogers F B, Cipolle M D, Velmahos G, et al. Practice management guidelines for the prevention of venous thromboembolism in trauma patients: the East practice management guidelines work group. J. Trauma 2002; 53:142-164.
Rosenthal D, Wellons E D, Lai K M, et al. Retrievable inferior venal cava filters: initial clinical results. Ann Vasc Surg 2006; 20:157-165.
Gosin I S, Graham A M, Ciocca R G, et al. Efficacy of prophylactic vena cava filters in high risk trauma patients. Ann Vasc Surg 1997; 11:100-105.

Spain D A, Richardson J D, Polk H C, et al. Routine prophylactic vena cava filter insertion in severely injured patients decreases the incidence of pulmonary embolism. J Am Coll Surg 1995; 180:641-647.
Stein P D, Kayali F, Olson R E. Twenty-one year trends in the use of inferior vena cava filters. Arch Intern Med 2004; 164:1541-1545.
Kaufman J A, Kinney T B, Streiff M D, et al. Guidelines for the use of retrievable and convertible vena cava filters: report from the Society of Interventional Radiology multidisciplinary consensus conference. J Vasc Intery Radiol. 2006; 17:449-459.
Rodriquez J L, Lopez J M, Proctor M C, et al. Early placemen of prophylactic vena cava filters in injured patients at high risk for pulmonary embolism. J. Trauma. 1996; 40:797-804.
Langan E M III, Miller R S, Caset W J III, Carsten C G III, Graham R M, Taylor S M. Prophylactic inferior vena cava filters in trauma patients at high risk: follow-up examination and risk/benefit assessment. J Vasc Surg. 1999; 30:484-490.
Greenfield L J, Proctor M C, Rodriquez J L, Luchette F A, Cipolle M D, Cho J. Posttrauma thromboembolism prophylaxis. J. Trauma. 1997, 42:100-103.
Young T, Tang H, Hughes R. Vena cava filters for the prevention of pulmonary embolism (Review). The Cochrane Library 2010, Issue 2.
Decousus H, Leizorovics A, Parent F, et al. A clinical trial of vena caval filters in the prevention of pulmonary embolism in patients with proximal deep-vein thrombosis, N England J. Med. 338, 7:409-415.
The PREPIC Study Group. Eight-year follow-up of patients with permanent vena cava filters in the prevention of pulmonary embolism: the PREPIC randomized study. Circulation 2005; 112:416-422.
Ray C E, Kaufman J A. Complications of vena cava filters. Abdom Imaging 1996; 21:368-374.
Ballew K A, Philbrick J T, Becker D M. Vena cava filter devices. Clin Chest Med 1995; 16:295-305.
Streiff M B. Vena cava filters: a comprehensive review. Blood 2000; 95:3669-3677.
Pons M, Riglietti A, van den Berg J C. The role of vena cava filters in the management of venous thromboembolism. J Cardiovasc Surg 2010; 51: 355-364.
Usoh F, Flignorani A, Ascher E, et al. Long-term follow-up for superior vena cava filter placement. Ann Vasc Surg. 2009; 23:350-354.
Turba U C, Arsian B, Meuse M, et al. Gunther Tulip filter retrieval experience: predictors of successful retrieval. Cardiovasc Intervent Radiol. 2009.
Kinney T B. Update on inferior vena cava filters. J Vasc Intery Radiol. 2003; 14:425-440.
Grande W J, Trerotola S O, Reilly P M, et al. Experience with the recovery filter as a retrievable inferior vena cava filter. J Vasc Intery Radiol 2005; 16:1189-1193.
Kirilcuk N N, Herget E J, Dicker R A, et al. Are temporary inferior vena cava filters really temporary? Am J Surg 2005; 190:858-863.
Kumar B C, Chakraverty Z, Zealley I. Failed retrieval of potentially retrievable IVC filters: a report of two cases. Cardiovasc Intervent Radiol 2006; 29: 126-127.
Removing Retrievable Inferior Vena Cava Filters: Initial Communication. FDA Division of Small Manufacturers, International and Consumer Assistance, Aug. 9, 2010.
Nicholson W, Nicholson W J, Tolerico P, et al. Prevalence of fracture and fragment embolization of Bard retrievable vena cava filters and clinical implications including cardiac perforation and tamponade. Arch Intern Med. 2010, pp. 1827-1831.
Karmy-Jones R, Jurkovich G H, Velmahos G C, et al. Practice patterns and outcomes of retrievable vena cava filters in trauma patients: an AAST multicenter study. J. Trauma. 2007; 62: 17-25.
Tschoe M, Kim H S, Brotman D J, et al. Retrievable vena cava filters: a clinical review. J Hosp Med 2009, 4; 7: 441-448.

\* cited by examiner

ABSORBABLE VASCULAR FILTER

RELATED APPLICATIONS

This application is a continuation application of and claims priority to application Ser. No. 13/036,351, filed Feb. 28, 2011, which application is expressly incorporated herein by reference in its entirety.

FIELD OF THE INVENTION

The present invention relates generally to a vascular filter and more particularly to an absorbable vascular filter deployed within a vessel for temporary filtering of body fluids. A preferred embodiment is the placement of such absorbable vascular filter within the inferior vena cava (IVC) for the prevention of pulmonary embolisms for a specific duration of time determined by the absorption properties of the filter.

BACKGROUND OF THE INVENTION

Between 100,000 to 300,000 Americans die annually from pulmonary embolism (PE)—more than breast cancer and AIDS combined—representing the 3rd leading cause of death in the US [1-5]. A similar incidence of PE is found in Europe with approximately 370,000 annual deaths [6]. Moreover, PE is the 3rd most common cause of death in trauma patients that survive the first 24 hours. An estimated 25% of all hospitalized patients have some form of deep vein thrombosis (DVT) which is often clinically unapparent unless PE develops [7]. On average, 33% of DVT will progress to symptomatic PE of which 10% will be fatal [6].

The US Surgeon General has recognized this alarming statistic and in 2008 issued a formal Call to Action to Prevent DVT and PE [1]. Unfortunately, DVT/PE disproportionately affects the elderly, in part due to prolonged periods of inactivity following medical treatment. The incidence is relatively low under the age of 50 (1/100,000), then accelerates exponentially reaching 1000/100,000 by the age of 85 [8]. Consequently the US Surgeon General has proclaimed that the growth in number of DVT/PE cases with an aging US population may outpace the population growth in the absence of better prevention [1].

Risk factors for PE arising from DVT follow Virchow's Triad [9]: (i) endothelial injury, (ii) hypercoaguability, and (iii) hemodynamic changes (stasis or turbulence). Hence specific risk factors include hip and knee arthroplasty, abdominal, pelvic and extremity surgeries, pelvic and long bone fractures, prolonged immobility such as prolonged hospital stays and air travel, paralysis, advanced age, prior DVT, cancer, obesity, COPD, diabetes and CHF. Orthopedic surgeons are especially concerned since their patients carry a 40%-80% risk for DVT and PE following knee and hip surgeries in the absence of prophylactic treatment [10-12].

The American Academy of Orthopaedic Surgeons (AAOS) has issued guidelines for PE prophylaxis. Basically, patients at standard risk should be considered for chemoprophylactic agents such as aspirin, low molecular weight heparin (LMWH), synthetic pentassaccharides, or warfarin, in addition to intra-operative and/or immediate postoperative mechanical prophylaxis [13].

Aspirin has a 29% relative risk reduction in symptomatic DVT and a 58% relative risk reduction in fatal PE [14]. LMWH carries a 30% risk reduction in DVT and has been proven more effective than unfractionated heparin in high risk groups such as hip and knee arthroplasty [7]. Warfarin started within 24 to 48 hours of initiating heparin with a goal of achieving international normalized ratio (INR) results between 2 and 3 as secondary thromboprophylaxis for 3 months reduces the risk of recurrent venous thromboembolism (VTE) by 90% as compared with placebo [15, 16]. Mechanical prophylaxis, consisting of pneumatic compression devices that repeatedly compress the legs with an air bladder, are also utilized in conjunction with anticoagulants to reduce the occurrence of PE.

The duration of prophylaxis depends on the source of potential DVT. Current recommendations for prophylaxis consist of a minimum 7 days and up to 30 days for many orthopedic surgeries. Specifically for orthopedic trauma, DVT prophylaxis is continued until patient mobilization (32%), inpatient discharge (19%), 3 weeks postop (16%), 6 weeks postop (27%), and in rare circumstances greater than 6 weeks (7%) [17]. Studies indicate that hypercoaguability persists for at least one month after injury in 80% of trauma patients [18]. Regarding total knee and hip arthroplasty and cancer surgeries, 35 day prophylactic treatment is recommended [12, 19]. Overall, prophylactic treatment for possible VTE is often warranted for up to 6 weeks following trauma or major surgery.

Contraindications for chemoprophylaxis include active bleeding, hemorrhagic diathesis, hemorrhagic stroke, neurologic surgery, excessive trauma, hemothorax, pelvic or lower extremity fractures with intracranial bleeding, anticoagulation interruption, and recent DVT/PE patients undergoing surgery.

For patients who are contraindicated for the above-mentioned anti-coagulation prophylaxis, or where anti-coagulation therapy has failed, the AAOS, American College of Physicians, and the British Committee of Standards in Haematology all recommend the use of inferior vena cava (IVC) filters [13, 20, 21]. These intravascular metal filters are deployed via catheter into the IVC to essentially catch emboli arising from DVT before reaching the lungs resulting in PE. Furthermore, the British Committee of Standards in Hematology recommends IVC filter placement in pregnant patients who have contraindications to anticoagulation and develop extensive VTE shortly before delivery (within 2 weeks).

The Eastern Association for Surgery of Trauma further recommends prophylactic IVC filters placed in trauma patients who are at increased risk of bleeding and prolonged immobilization [22]. Such prophylactic recommendation follows studies that demonstrate a low rate of PE in patients with severe polytrauma who underwent IVC placement [23-25]. In fact the fastest growing indication of overall IVC filter usage, from 49,000 in 1999 to 167,000 in 2007 with a projected 259,000 units for 2012, is the prophylactic market utilizing retrievable IVC filters [26, 27].

Example vascular filters primarily for IVC placement are disclosed in U.S. Pat. Nos. 4,425,908; 4,817,600; 5,626,605; 6,146,404; 6,217,600 B1; 6,258,026 B1; 6,497,709 B1; 6,506,205 B2; 6,517,559 B1; 6,620,183 B2; U.S. Pat. App. Pub. No. 2003/0176888; U.S. Pat. App. Pub. No. 2004/0193209; U.S. Pat. App. Pub. No. 2005/0267512; U.S. Pat. App. Pub. No. 2005/0267515; U.S. Pat. App. Pub. No. 2006/0206138 A1; U.S. Pat. App. Pub. No. 2007/0112372 A1; U.S. Pat. App. Pub. No. 2008/0027481 A1; U.S. Pat. App. Pub. No. 2009/0192543 A1; U.S. Pat. App. Pub. No. 2009/0299403 A1; U.S. Pat. App. Pub. No. 2010/0016881 A1; U.S. Pat. App. Pub. No. 2010/0042135 A1; and U.S. Pat. App. Pub. No. 2010/0174310 A1.

IVC filter efficacy has been demonstrated in several class I and II evidence studies [22, 28-30]. Most of the earlier filters installed were expected to be permanent fixtures since endothelialization occurs within 7-10 days making most models impractical to remove without irreversible vascular damage leading to life threatening bleeding, dissection of the IVC, and thrombosis. Although these permanent filters have prevented PE, they have been shown to actually increase the risk of recurrent DVT over time.

Specifically, a Cochrane review [31] on the use of IVC filters for the prevention of PE cites a level I randomized prospective clinical trial by Decousus et al. [32] wherein the incidence of DVT with the IVC filter cohort increased almost 2-fold: (i) 21% incidence of recurrent DVT in the filter cohort vs. 12% in the non-filter LMWH cohort at 2 years (p=0.02), and (ii) 36% incidence of recurrent DVT in the filter cohort vs. 15% in the non-filter group at 8 years (p=0.042) [33]. However, the filters did reduce the occurrence of PE; the filter cohort experiencing only 1% PE vs. the non-filter cohort posting 5% PE in the first 12 days (p=0.03). No statistically significant difference in mortality rate was seen in any time frame investigated. Apparently the initial benefit of reduced PE with permanent IVC filters is offset by an increase in DVT, without any difference in mortality.

In addition to increased incidence of DVT for prolonged IVC filter deployment, filter occlusion has been reported with a 6% to 30% occurrence, as well as filter migration (3% to 69%), venous insufficiency (5% to 59%), and post thrombotic syndrome (13% to 41%) [34-36]. Complications from insertion including hematoma, infection, pneumothorax, vocal cord paralysis, stroke, air embolism, misplacement, tilting arteriovenous fistula, and inadvertent carotid artery puncture have an occurrence rate of 4%-11% [37].

Temporary or retrievable IVC filters have been marketed more recently intended to be removed once the risk of PE subsides, and hence circumvent many of the deleterious complications of permanent filters. The retrievable filters feature flexible hooks, collapsing components, and unrestrained legs to ease retrieval. Unfortunately these same features have led to unwanted filter migration, fatigue failure, IVC penetration, fragment migration to hepatic veins and pulmonary arteries, filter tilt, and metallic emboli [38-43]. Since 2005, 921 adverse filter events have been reported to the FDA including 328 device migrations, 146 device detachments (metallic emboli), 70 perforations of the IVC, and 56 filter fractures [44]. Some retrievable brands post alarming failure rates such as the Bard Recovery filter with 25% fracturing over 50 months which embolized end organs. 71% of the fractures embolized to the heart caused life threatening ventricular tachycardia, tamponade, and sudden death in some cases. An alternative retrievable model, Bard G2, resulted in 12% fractures over 24 months [45]. Such prevalence of device fractures is postulated to be directionally proportional to indwell time.

These failures and others prompted the FDA in August 2010 to issue a formal communication stating that "FDA recommends that implanting physicians and clinicians responsible for the ongoing care of patients with retrievable IVC filters consider removing the filter as soon as protection from PE is not longer needed" [44]. Even though these types of retrievable filters are intended to be removed in months time, several studies indicate that approximately 70%-81% of patients with retrievable IVC filters fail to return to the hospital for filter removal, thereby exposing hundreds of thousands of patients to the life-threatening adverse events of prolonged retrievable IVC filter placement [41, 44, 46-48]. These patients are either lost to follow-up, or refuse to have the filters removed in the absence of complications.

BRIEF SUMMARY OF THE INVENTION

The present invention comprises systems and methods for filtering fluids. Certain embodiments comprise a novel absorbable vascular filter that temporarily prevents pulmonary embolism by capturing and restraining emboli within a body vessel. The absorbable vascular filter, according to certain aspects of the invention, possesses various advantages over all conventional vascular filters, including permanent, temporary, and optional IVC filters. Most importantly, the absorbable vascular filter disclosed herein is slowly biodegraded in a sequential manner within the vessel according to a planned schedule engineered by the choice of absorbable filter materials which prevents the requirement of filter removal. Moreover, the absorbable vascular filter elements are manufactured from non-metallic synthetic polymers which do not adversely impact end organs upon carefully planned degradation as exhibited by conventional metal IVC filters that migrate and often become fractionated. Also due to the relative short indwell time (months) of the absorbable vascular filter, the paradoxical increase in DVT seen with conventional long-term IVC filters is likely circumvented.

BRIEF DESCRIPTION OF THE DRAWINGS

FIG. 2b is an enlarged end-view of the absorbable capture elements of the absorbable filter depicted in FIG. 2a.

DETAILED DESCRIPTION OF THE INVENTION

Embodiments of the present invention will now be described in detail with reference to the drawings, which are provided as illustrative examples so as to enable those skilled in the art to practice the invention. Notably, the figures and examples below are not meant to limit the scope of the present invention to a single embodiment, but other embodiments are possible by way of interchange of some or all of the described or illustrated elements. Wherever convenient, the same reference numbers will be used throughout the drawings to refer to same or like parts. Where certain elements of these embodiments can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the components referred to herein by way of illustration.

Figures 1A, 1B, 1C, 1D, 1E:
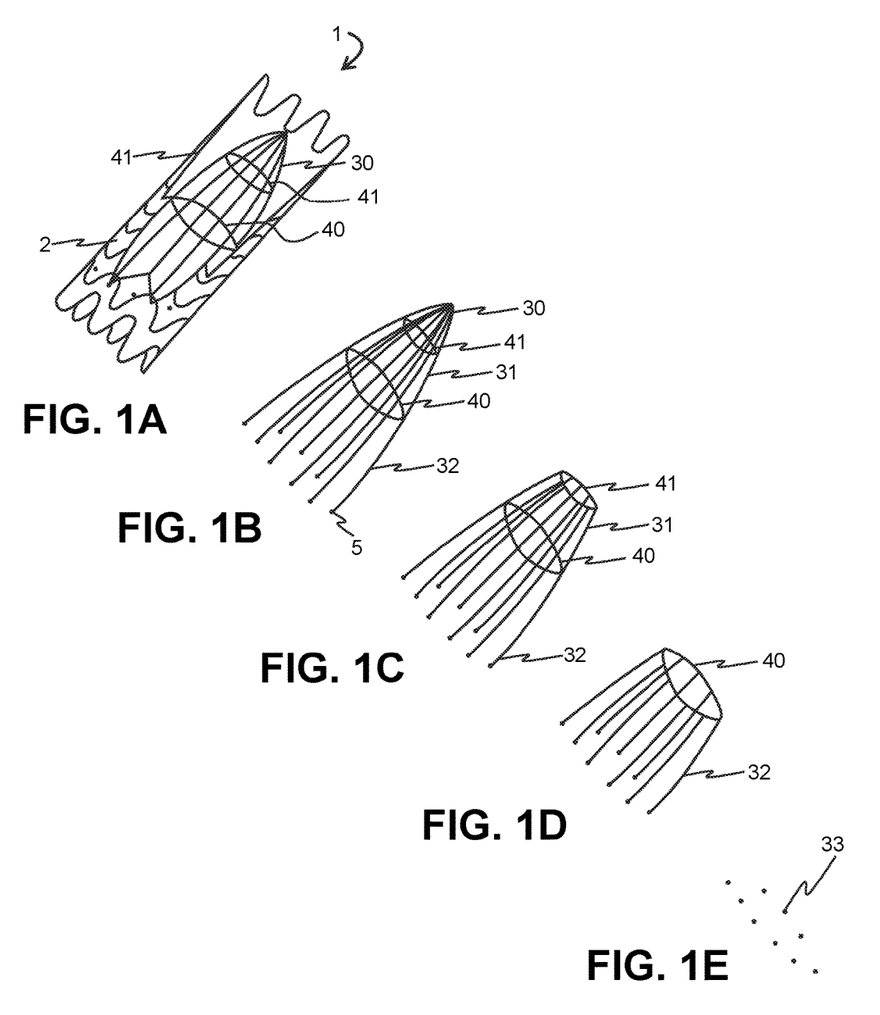
FIG. 1a is a cut-away isometric view of one embodiment of the absorbable vascular filter that includes phased sequential biodegradation of the absorbable capture elements.
FIG. 1b features the capture elements of FIG. 1a in detail.
FIG. 1c features the capture elements of FIG. 1b at a later point in time wherein the proximal portion of the capture elements has been bioabsorbed/biodegraded.
FIG. 1d features the capture elements of FIG. 1c at a later point in time wherein the proximal and middle sections of the capture elements have been bioabsorbed/biodegraded, leaving only the distal section.
FIG. 1e represents complete bioabsorption/biodegradation of the capture elements of FIG. 1b at the most distant point in time.

Referring to the embodiment depicted in FIGS. 1a-e, an absorbable vascular filter 1 consists of an outer, circumferential element 2 for supporting a plurality of absorbable filter capture elements (30-32, 40-41). The capture elements are purposely designed to be biologically absorbed and/or degraded in a sequential manner to avoid simultaneous detachment of the entire filter causing an unexpected embolus. The sequential bioabsorption/biodegradation is illustrated in FIGS. 1b-e where decomposition begins with the proximal capture elements 30, progressing to the middle section capture elements 31, and finally full bioabsorption/biodegradation as depicted in FIG. 1e.

Such engineered, sequential bioabsorption/biodegradation of the capture elements can be achieved with numerous synthetic materials. The goal is to select the absorbable filter materials to match a desired filter indwell time. Per the prior background section, a filter indwell time of 6 weeks would be suitable for an IVC filter to prevent PE following trauma or in conjunction with major surgeries. Plausible synthetic materials include:

Polydioxanone (PDO, PDS)—colorless, crystalline, biodegradable synthetic polymer of multiple repeating ether-ester units. In suture form, PDS II (Ethicon, Somerville, N.J.) size 4/0 and smaller maintains 60%, 40%, and 35% of its tensile strength at 2, 4, and 6 weeks respectively. For PDS II size 3/0 and larger, it retains 80%, 70%, and 60% of its tensile strength at 2, 4, and 6 weeks respectively. In addition to providing wound support for 6 weeks, PDS II suture is fully absorbed in 183-238 days via hydrolysis making it a strong candidate for IVC filter applications. Basically absorption is minimal in the first 90 days and is essentially complete in 6 months. Finally, PDS has a low affinity for microorganisms and possesses minimal tissue reaction.

Polytrimethylene carbonate (Maxon)—similar to PDS in absorption profile yet with slightly higher breaking strength. Maxon (Covidien, Mansfield, Mass.) maintains 81%, 59%, and 30% of its tensile strength at 2, 4, and 6 weeks respectively, and is fully hydrolyzed in 180-210 days.

Polyglactin 910 (Vicryl)—braided multifilament coated with a copolymer of lactide and glycolide (polyglactin 370). In suture form, Vicryl (Ethicon) size 6/0 and larger maintains 75%, 50%, and 25% of its tensile strength at 2, 3, and 4 weeks respectively and is fully absorbed in 56-70 days.

Polyglycolic acid (Dexon)—similar to Polyglactin, made from polyglycolic acid and coated with polycaprolate. Dexon has similar tensile strength and absorption profile as Polyglactin.

Poliglecaprone 25 (Monocryl)—synthetic copolymer of glycolide and e-caprolactone. Monocryl (Ethicon) maintains 50%-70% and 20%-40% of its tensile strength at 1 and 2 weeks respectively and is fully absorbed in 91-119 days.

Polylacticoglycolic acid (PLGA) copolymer of monomers glycolic acid and lactic acid. Different forms and properties of PLGA can be fabricated by controlling the ratio of lactide to glycolide for polymerization. Like the other synthetic absorbable materials, PLGA degrades by hydrolysis with the absorption profile dependent on the monomer ratio; the higher content of glycolide, the faster degradation. However, the 50:50 copolymer exhibits the fastest degradation at 2 months. Since the polymer degrades in the body to produce lactic acid and glycolic acid, both being normal physiological substances, PLGA poses minimal systemic toxicity.

As a specific example of engineering capture elements to sequentially degrade following the period of PE protection, the proximal capture elements 30, 41 could be fabricated with PDS II size 4/0 (0.15 mm dia.), while the middle capture elements 31, 40 fabricated with size 2/0 (0.3 mm dia.), and finally the distal capture elements 32 fabricated with size 2 (0.5 mm) PDS II suture.

As an alternative to assembling a plurality of capture elements, the vascular filter can be fabricated with absorbable or non-absorbable composite mesh. Candidates for a mesh capture system include polypropylene such as C-QUR™ (Atrium Medical Corp. Hudson N.H.), polypropylene encapsulated by polydioxanone as in PROCEED® (Ethicon, Somerville, N.J.), polypropylene co-knitted with polyglycolic acid fibers as in Bard Sepramesh™ IP Composite (Davol, Inc., Warwick, R.I.), polyethylene terephathalate as in Parietiex™ Composite (Covidien, Mansfield, Mass.), and ePTFE used in DUALAMESH® (W. Gore & Assoc. Inc., Flagstaff, Ariz.).

Regarding the circumferential element 2 in FIGS. 1 and 2 that serves to support the capture elements of the absorbable vascular filter and maintain filter positioning within the vessel upon expansion, either an absorbable material such as described above or non-absorbable material can be utilized. A non-absorbable material would essentially serve as a permanent stent, lasting well beyond the life of the absorbable capture elements. This may be an important option in cases where the vessel needs assistance in maintaining patency. Both types of circumferential elements 2 would likely incorporate barbs 79 (refer FIG. 2) to maintain filter positioning upon deployment. Plausible non-absorbing materials for constructing the circumferential element include: Nitinol, Elgiloy, Phynox, 316 stainless steel, MP35N alloy, titanium alloy, platinum alloy, niobium alloys, cobalt alloys, and tantalum wire.

Figure 2A:
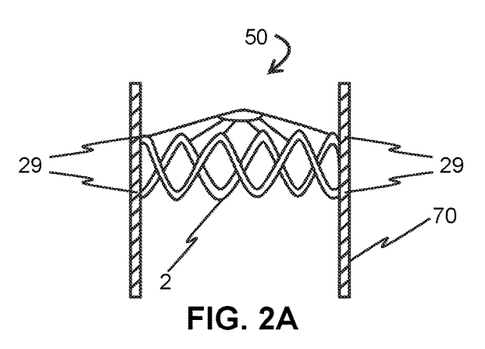
FIG. 2a is a cross-sectional schematic of another embodiment of the absorbable vascular filter that also features phased sequential biodegradation of the absorbable capture elements.
Figure 2B:
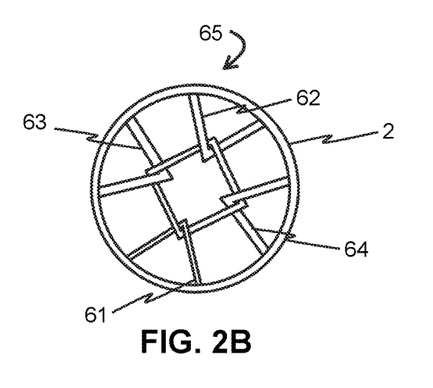
Figures 2C, 2D:
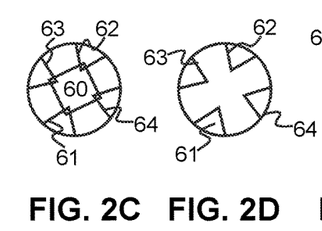
FIG. 2c depicts the capture elements of FIG. 2b at the time of filter installation in a vessel.
FIG. 2d depicts the capture elements of FIG. 2c at a later point in time wherein the inner capture ring element has been bioabsorbed/biodegraded.
Figures 2E, 2F:
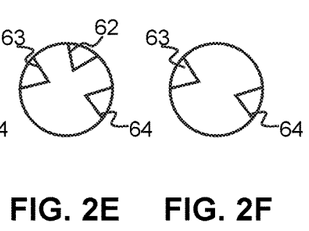
FIG. 2e depicts the capture elements of FIG. 2d at a later point in time wherein a circumferential-mounted capture element has been bioabsorbed/biodegraded.
FIG. 2f depicts the capture elements of FIG. 2e at a later point in time wherein two circumferential-mounted capture elements have been bioabsorbed/biodegraded.
Figure 2G:
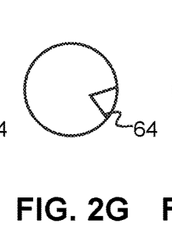
FIG. 2g depicts the capture elements of FIG. 2f at a later point in time wherein only one circumferential-mounted capture element remains following bioabsorption/biodegradation.
Figure 2H:
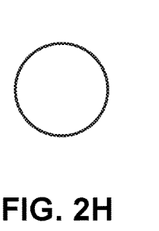
FIG. 2h depicts the capture elements of FIG. 2b which have completely been bioabsorbed/biodegraded at the most distant point in time.

FIGS. 2a-2h illustrate another embodiment of the absorbable vascular filter wherein the absorbable capture elements 60-64 are mounted to a simple circumferential element 2 held against the vessel wall 70 with barbs 79. Here again the circumferential element 2 can be fabricated with absorbable or non-absorbable materials of the like described above. An enlarged cross-sectional view of the capture element assembly 65 is shown in FIG. 2b. Notice that the sequential degradation of the capture elements is achieved by varying the diameter of the chosen absorbable material. For example, the inner capture element 60 could be PDS II 4/0 (0.15 mm dia.) resulting in the fastest absorption as illustrated in FIG. 2d at time $t_1$, followed by capture element 61 degradation being PDS II 3/0 (0.20 mm dia.) at time $t_2$ in FIG. 2e, followed by capture element 62 degradation being PDS II 2/0 (0.30 mm dia.) at time $t_3$ in FIG. 2f, followed by capture element 63 degradation being PDS II 0 (0.35 mm dia.) at time $t_4$ in FIG. 2g, and finally the degradation of the last capture element 64 constructed of PDS II 1 (0.40 mm dia.) at time $t_5$ in FIG. 2h. Overall, a gradual progression of degradation is designed purposely following a prophylactic window of 6 weeks for trauma and major surgery applications.

Figures 3A, 3B, 3C, 3D:
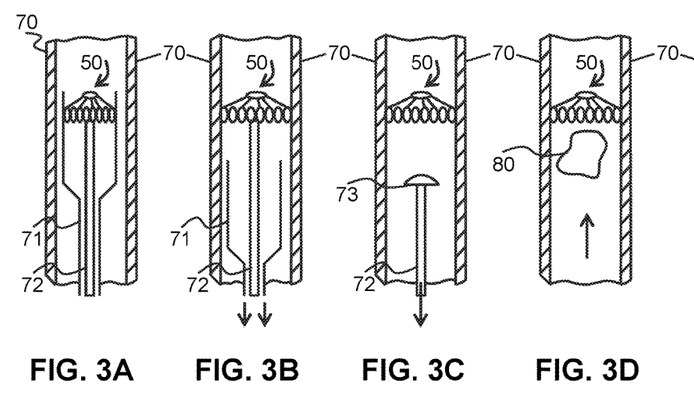
FIG. 3a is a cross-sectional schematic revealing a preferred method for installing the absorbable vascular filter using a catheter-based system with the filter in compressed mode.
FIG. 3b is a cross-sectional schematic detailing the deployment of the absorbable vascular filter using a catheter-based system with sliding outer sheath to deploy the filter in the fully expanded mode.
FIG. 3c is a cross-sectional schematic detailing the removal of the central stabilizing rod used to stabilize the absorbable vascular filter while removing the outer sheath of the catheter-based installation system.
FIG. 3d illustrates the operation of the absorbable vascular filter in the presence of an embolus in the vessel.
Figure 3E:
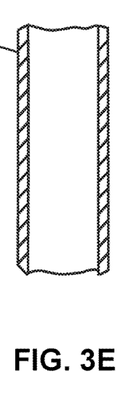
FIG. 3e represents the vessel following complete biodegradation/bioabsorption of the absorbable vascular filter.

A preferred installation of the absorbable vascular filter is via intravenous insertion with a catheter requiring only a local anesthetic as illustrated in FIGS. 3a-e. Here the filter is collapsed and compressed within a delivery catheter comprised of an outer sheath 71 and internal applicator or stabilizer 73 on a central rod 72 as illustrated in FIG. 3a. For IVC filter deployment, the delivery catheter is inserted into the patient's vasculature of convenient location, such as the femoral vein. Subsequently, the delivery catheter is fed through the vasculature until reaching the desired deployment location, typically just inferior to the renal veins. Next the compressed filter 50 is allowed to expand upon sliding the exterior sheath 71 in the distal direction while simultaneously holding the stabilizer rod 72 steady (refer FIG. 3b). Once the exterior sheath 71 is withdrawn distally away from the filter, the stabilizing rod 73 can also be retracted distally as depicted in FIG. 3c. Consequently as a thrombosis event releases an embolus 80, the embolus is captured by the absorbable vascular filter and is prevented from traveling to the heart and lungs thereby preventing a potentially fatal PE (refer FIG. 3d). Following the desired prophylactic time window for filter utilization (approximately 6 weeks in many applications), the filter is biologically absorbed resulting in the absence of any foreign material in the vessel as depicted in FIG. 3e.

Although the present invention has been described with reference to specific exemplary embodiments, it will be evident to one of ordinary skill in the art that various modifications and changes may be made to these embodiments without departing from the broader spirit and scope of the invention. Accordingly, the specification and drawings are to be regarded in an illustrative rather than a restrictive sense.

REFERENCES

[1] Goldhaber S Z, Ortel T L. The Surgeon General's Call to Action to Prevent Deep Vein Thrombosis and Pulmonary Embolism, Office of the Surgeon General (US), National Heart, Lung, and Blood Institute (US). Rockville (Md.). 2008
[2] Spencer F A, Emery C, Lessard D, Anderson F, Emani S, Aragam J et al. The Worcester Venous Thromboembolism study; a population-based study of the clinical epidemiology of venous thromboembolism. J Gen Intern Med 2006 July; 21 (7); 722-7.
[3] Bick R L. Hereditary and acquired thrombophilia: preface. Semin Thromb Hemost 1999; 25; 251-3.
[4] Agudelo J F, Morgan S J, Smith W R. Venous Thromboembolism in Orthopedic Trauma Patients, Orthopedics. 2005 October; 28(10):1164-71.
[5] Tapson V F. Acute pulmonary embolism. N Engl J Med, 2008, 358, 10. 1037-52.
[6] Goldhaber S Z, Visani L, De Rosa M. Acute PE: clinical outcomes in the International Cooperative PE Registry (ICOPER). Lancet 1999. 353. 1386-9.
[7] Geerts W H, Jay R M, Code K l, et al. A comparison of low-dose heparin with low-molecular weight heparin as prophylaxis against venous thromboembolism after major trauma. N Engl J Med. 1996; 335:701-7.
[8] Silverstein D M, Heit J A, Mohr D N, Petterson T M, O'Fallon W M, Meltron L J, $3^{rd}$. Trend s int eh incidence of deep vein thrombosis and pulmonary embolism: a 25-year population-based study. Arch Intern Med 1998; 158(6). 585-93.
[9] Von V R. Weitere untersuchungen ueber die verstopfung der lungenarterien und ihre folge. Traube's Beitraege exp Path u Physiol, 1846; 2:21-31.
[10] Goldhaber S Z, Savage D D, Garrison R J, et al. Risk factors for pulmonary embolism: The Framingham Study. Am J Med. 1983; 74: 1023-1028.
[11] Coon W W. Epidemiology of venous thromboembolism. Ann Surg. 1977; 186:149-164.
[12] Muntz J E, Michota F A. Pervention and management of venous thromboembolism in the surgical patient: options bye surgery type and individual patient risk factors, Am J of Surg, 2010; 199, S11-20.
[13] American Academy of Orthopaedic Surgeons Clinical Guideline on Prevention of Pulmonary Embolism in Patients Undergoing Total Hip or Knee Arthroplasty, American Academy of Orthopaedic Surgeons, May 2007.
[14] Pulmonary Embolism Prevention (PEP) Trial Collaborative Group: Prevention of pulmonary embolism and DVT with low dose aspirin: pulmonary embolism prevention (PEP) trial. Lancet. 2000; 355: 1295-1302
[15] Prins M H, Hutten B A, Koopman M M, et al. Longterm treatment of venous thromboembolic disease. Thromb Haemost 1999; 82:892-8.
[16] Tran H, McRae S, Ginsberg J. Anticoagulant Treatment of Deep Vein Thrombosis and Pulmonary Embolism. Cardiology Clinics, 2008, 26, 235-50.
[17] Morgan S J, Jeray K J, Phieffer L S, Grisby J H, Bosse M J, Kellam J F. Attitudes of orthopaedic trauma surgeons regarding current controversies in the management of pelvic and acetabular fractures. J Orthop Trauma. 2001; 15:526-32.
[18] Meissner M H, Chandler W L, Elliot J S. Venous thromboembolism in trauma: a local manifestation of systemic hypercoagulability? J Trauma. 2003; 4:224-31.
[19] Geerts W H, Bergqvist D, Pineo G F, et al. Prevention of venous thromboembolism: American College of Chest Physicians evidence-based clinical practice guidelines (8th edition). Chest. 2008; 133:3815-4535.

[20] Huo M H, Spyropoulos A C. The eighth American college of chest physicians guidelines on venous thromboembolism prevention: implications for hospital prophylaxis strategies. J Thromb Thrombolysis. 2011, February; 31(2): 196-208.

[21] Baglin T P, Brush J, Streiff M. Guidelines on the use of vena cava filters. British Committee for Standard in Haematology, British J of Haematology, 2006, 134, 590-5.

[22] Rogers F B, Cipolle M D, Velmahos G, et al. Practice management guidelines for the prevention of venous thromboembolism in trauma patients: the East practice management guidelines work group. J Trauma. 2002; 53:142-164.

[23] Rosenthal D, Wellons E D, Lai K M, et al. Retrievable inferior venal cava filters: initial clinical results. Ann Vasc Surg 2006; 20:157-165.

[24] Gosin I S, Graham A M, Ciocca R G, et al. Efficacy of prophylactic vena cava filters in high risk trauma patients. Ann Vasc Surg 1997; 11:100-05.

[25] Spain D A, Richardson J D, Polk H C, et al. Routine prophylactic vena cava filter insertion in severely injured patients decreases the incidence of pulmonary embolism. J Am Coll Surg 1995; 180:641-47.

[26] Stein P D, Kayali F, Olson R E. Twenty-one year trends in the use of inferior vena cava filters. Arch Intern Med 2004; 164:1541-5.

[27] Kaufman J A, Kinney T B, Streiff M D, et al. Guidelines for the use of retrievable and convertible vena cava filters: report from the Society of Interventional Radiology multidisciplinary consensus conference. J Vasc Intery Radiol. 2006; 17:449-459.

[28] Rodriquez J L, Lopez J M, Proctor M C, et al. Early placemen of prophylactic vena cava filters in injured patients at high risk for pulmonary embolism. J Trauma. 1996; 40:797-804.

[29] Langan E M III, Miller R S, Caset W J III, Carsten C G III, Graham R M, Taylor S M. Prophylactic inferior vena cava filters in trauma patients at high risk: follow-up examination and risk/benefit assessment. J Vasc Surg. 1999; 30:484-90.

[30] Greenfield L J, Proctor M C, Rodriquez J L, Luchette F A, Cipolle M D, Cho J. Posttrauma thromboembolism prophylaxis. J Trauma. 1997, 42:100-03.

[31] Young T, Tang H, Hughes R. Vena cava filters for the prevention of pulmonary embolism (Review). The Cochrane Library 2010, Issue 2.

[32] Decousus H, Leizorovics A, Parent F, et al. A clinical trial of vena caval filters in the prevention of pulmonary embolism in patients with proximal deep-vein thrombosis, N England J Med. 338, 7:409-15.

[33] The PREPIC Study Group. Eight-year follow-up of patients with permanent vena cava filters in the prevention of pulmonary embolism: the PREPIC randomized study. Circulation 2005; 112:416-22.

[34] Ray C E, Kaufman J A. Complications of vena cava filters. Abdom Imaging 1996; 21:368-74.

[35] Ballew K A, Philbrick J T, Becker D M. Vena cava filter devices. Clin Chest Med 1995; 16:295-305.

[36] Streiff M B. Vena cava filters: a comprehensive review. Blood 2000; 95:3669-77.

[37] Pons M, Riglietti A, van den Berg J C. The role of vena cava filters in the management of venous thromboembolism. J Cardiovasc Surg 2010; 51: 355-64.

[38] Usoh F, Hignorani A, Ascher E, et al. Long-term follow-up for surperior vena cava filter placement. Ann Vasc Surg. 2009; 23:350-4.

[39] Turba U C, Arsian B, Meuse M, et al. Gunther Tulip filter retrieval experience: predictors of successful retrieval. Cardiovasc Intervent Radiol. 2009

[40] Kinney T B. Update on inferior vena cava filters. J Vasc Intery Radiol. 2003; 14:425-40.

[41] Grande W J, Trerotola S O, Reilly P M, et al. Experience with the recovery filter as a retrievable inferior vena cava filter. J Vasc Intery Radiol 2005; 16:1189-93.

[42] Kirilcuk N N, Herget E J, Dicker R A, et al. Are temporary inferior vena cava filters really temporary? Am J Surg 2005; 190:858-63.

[43] Kumar B C, Chakraverty Z, Zealley I. Failed retrieval of potentially retrievable IVC filters: a report of two cases. Cardiovasc Intervent Radiol 2006; 29: 126-7.

[44] Removing Retrievable Inferior Vena Cava Filters: Initial Communication. FDA Division of Small Manufacturers, International and Consumer Assistance, Aug. 9, 2010.

[45] Nicholson W, Nicholson W J, Tolerico P, et al. Prevalence of fracture and fragment embolization of Bard retrievable vena cava filters and clinical implications including cardiac perforation and tamponade. Arch Intern Med. 2010.

[46] Karmy-Jones R, Jurkovich G H, Velmahos G C, et al. Practice patterns and outcomes of retrievable vena cava filters in trauma patients: an AAST multicenter study. J Trauma. 2007; 62: 17-25.

[47] Tschoe M, Kim H S, Brotman D J, et al. Retrievable vena cava filters: a clinical review. J Hosp Med 2009, 4; 7: 441-8.

[48] Dabbagh O, Nagam N, Chitima-Matsiga R, et al. Retrievable inferior vena cava filters are not getting retrieved Where is the gap? Thrombosis Rsch 2010. 126: 493-7.

What is claimed is:

1. An absorbable filter configured for intra vena cava deployment comprising:
a rigid polymeric circumferential element for attaching the filter to a vessel, the circumferential element configured to provide sufficient radial force to maintain placement in the vessel; and
a plurality of absorbable capture elements affixed to the rigid polymeric circumferential element for capturing unwanted substances flowing in a vessel for a limited period of time,
wherein the circumferential element is characterized by a first lattice spacing and the plurality of absorbable capture elements are characterized by a second lattice spacing, the first lattice spacing formed by a sinusoidal circumferential element lattice, the second lattice spacing formed by a cross-sectional petal structure of the filter formed by the plurality of absorbable capture elements transverse to a longitudinal axis of the filter,
wherein individual ones of the plurality of absorbable capture elements are linked with adjacent absorbable capture elements via an absorbable inner capture element coupled with the plurality of absorbable capture elements to establish the second lattice spacing,
wherein the linking by the inner capture element creates a first portion of the cross-sectional petal structure between the plurality of absorbable capture elements having a plurality of first petals with a first petal spacing, and a second portion of the cross-sectional petal structure between the plurality of absorbable capture elements having a plurality of second petals with a second petal spacing, the plurality of absorbable capture elements extending from apexes of the sinusoidal circumferential element lattice toward the absorbable inner capture element, the plurality of absorbable capture elements configured such that the first portion of the cross-sectional petal structure and the second portion of the cross-sectional petal structure are located in a lumen of the vena cava to capture or retard the substances flowing in the vessel; and wherein the circumferential element, the plurality of absorbable capture elements, and the absorbable inner capture element are fully resorbable such that after a target prophylactic time window for filter utilization, these components are biologically absorbed, resulting in an absence of these filter components in the vessel, wherein the first and second portions of the cross-sectional petal structure do not extend past the inner capture element toward a radial center of the circumferential element, and the plurality of first and second petals loop through the inner capture element to integrate the first and second portions of the cross-sectional petal structure to form a capture basket.

2. A device as set forth in claim 1, wherein ends of the absorbable capture elements are attached to the apexes of the sinusoidal circumferential element lattice to form the first and second portions of the cross-sectional petal structure, such that collectively the first and second portions of the cross-sectional petal structure form a capture basket.

3. A device as set forth in claim 1, wherein a subset of the absorbable capture elements are chosen to sequentially degrade in time to avoid simultaneous bulk release of capture elements in the vessel over time.

4. A device as set forth in claim 1, wherein the plurality of absorbable capture elements are fabricated from absorbable materials chosen from a group including polydioxanone, polytrimethylene carbonate, polyglactin, polyglycolic acid, poliglecaprone, polyglytone, and polylacticoglycolic acid.

5. A device as set forth in claim 1, wherein the plurality of absorbable capture elements are absorbable sutures.

6. A device as set forth in claim 5, wherein the plurality of absorbable capture elements are constructed from absorbable sutures chosen from a group including Vicryl, Monocryl, PDS, PDS II, Dexon, Dexon II, Maxon, PLGA, Surgical Gut, Ethibond, Panacryl, and Caprosyn.

7. A device as set forth in claim 1, wherein the circumferential element is fabricated of absorbable materials chosen from a group including polydioxanone, polytrimethylene carbonate, polyglactin, polyglycolic acid, poliglecaprone, polyglytone, and polylacticoglycolic acid.

8. A device as set forth in claim 1, wherein the circumferential element comprises an anchor element or barb for attachment to a vessel.

9. An absorbable filter comprising:
a circumferential element attached to a vessel; and
a capture basket affixed to the circumferential element for capturing unwanted substances flowing in a vessel for a limited period of time,
wherein the circumferential element is characterized by a first lattice spacing and the capture basket is characterized by a second lattice spacing, the first lattice spacing formed by a sinusoidal circumferential element lattice, the second lattice spacing formed by a cross-sectional petal structure of the filter formed by the capture basket transverse to a longitudinal axis of the filter,
wherein the capture basket comprises a plurality of absorbable capture elements and an absorbable inner capture element configured to link the plurality of absorbable capture elements to establish the second lattice spacing,
wherein linking of the plurality of absorbable capture elements by the inner capture element creates a first portion of the cross-sectional petal structure between the plurality of absorbable capture elements having a plurality of first petals with a first petal spacing, and a second portion of the cross-sectional petal structure between the plurality of absorbable capture elements having a plurality of second petals with a second petal spacing, the plurality of absorbable capture elements extending from apexes of the sinusoidal circumferential element lattice toward the absorbable inner capture element, the plurality of absorbable capture elements configured such that the first portion of the cross-sectional petal structure and the second portion of the cross-sectional petal structure are located in a lumen of the vena cava to capture or retard the substances flowing in the vessel, and
wherein the circumferential element, the capture basket including the plurality of capture elements, and the absorbable inner capture element are fully resorbable such that after a target prophylactic time window for filter utilization, these components are biologically absorbed, resulting in an absence of these filter components in the vessel, wherein the first and second portions of the cross-sectional petal structure do not extend past the inner capture element toward a radial center of the circumferential element, and the plurality of first and second petals loop through the inner capture element to integrate the first and second portions of the cross-sectional petal structure to form a capture basket.

10. A device as set forth in claim 9, wherein the capture basket is a mesh.

11. A device as set forth in claim 10, wherein the capture basket is fabricated from materials chosen from a group including polypropylene, polypropylene encapsulated in polydioxanone, polypropylene co-knitted with polyglycolic acid fibers, polyethylene terephathalate, and ePTFE.

12. A device as set forth in claim 10, wherein the capture basket is fabricated from materials chosen from a group including polypropylene as in C-QUR™, polypropylene encapsulated by polydioxanone as in PROCEED®, polypropylene co-knitted with polyglycolic acid fibers as in Bard Sepramesh™ IP Composite, polyethylene terephathalate as in Parietiex™ Composite, and ePTFE as in DUALAMESH®.

13. A method for delivering a filter as claimed in 1 or claim 9 with a delivery catheter, wherein the delivery comprises:
inserting the filter, in compressed form, within a delivery catheter through the femoral or jugular vein to a desired position within a vessel at or near a vena cava; and
deploying the filter in expanded form at the desired position within a vessel; and
subsequently removing the delivery catheter from the vessel back through the femoral or jugular vein.

* * * * *